US005879674A

United States Patent [19]
Black
[11] Patent Number: 5,879,674
[45] Date of Patent: Mar. 9, 1999
[54] POTENTIATION OF EPIZOOTIC VIRAL INFECTIONS OF INSECTS
[75] Inventor: Bruce Christian Black, Yardley, Pa.

[73] Assignee: American Cyanamid Company, Parsippany, N.J.

[21] Appl. No.: 837,503

[22] Filed: Feb. 18, 1992

[51] Int. Cl.[6] .................................................... A01N 63/00

[52] U.S. Cl. ............................... 424/93.6; 424/405; 8/648

[58] Field of Search ................................. 424/93 T, 93.6, 424/405

[56] References Cited

U.S. PATENT DOCUMENTS

| | | | |
|---|---|---|---|
| 4,911,913 | 3/1990 | Hostetter et al. | 424/93 T |
| 5,023,182 | 6/1991 | Vail et al. | 424/93 T |
| 5,124,149 | 6/1992 | Shapiro et al. | 424/93 T |
| 5,132,220 | 7/1992 | Shapiro et al. | 424/93 T |

FOREIGN PATENT DOCUMENTS

| | | | |
|---|---|---|---|
| 2552627 | 4/1985 | France | 424/93 T |

OTHER PUBLICATIONS

US Agric. Res. Ser. Doc. No. 91–171487/23, Pat. Appl. 7–609,848/WGI, Shapiro et al., Compositions and Methods for Biocontrol Using Fluorescent Brighteners.

R.P. Jaques, The inactivation of the nuclear polyhedrosis virus of *Trichoplusia ni* by gamma and ultraviolet radiation, Canadian J. Microbiology, vol. 14, pp. 1161–1163 (1968).

Martignoni et al., Lab. Eval. of New UV Absorbers for Protection of Douglas–fir Tussock Moth . . . *Baculovirus,* J. Econ. Entomol., vol. 78, pp. 982–987 (1985).

R.F. Chapman, The Insects: Structure and Function, 2d ed., p. 46 (American Elsevier Publishing Co., Inc. (1971)).

Doane et al., Enhancement of the Action of *Bacillus thuringiensis* . . . on *Porthetria dispar* . . . , J. Insect Pathology, vol. 6, pp. 423–429 (1964).

Holt et al., Fluorescent Whitening Agents. II. Covalent Binding to Proteins during Irradiation by Sunlight, Aust. J. Biol. Sci., vol. 27, pp. 23–29 (1974).

Milligan et al., Fluorescent Whitening Agents. I. Bis–4, 4'–( . . . –phenoxy–s–triazin–2"–ylamino) stilbene–2,2'–disulphonic Acid: Its Photodecomposition in Solution and on Wool, Aust. J. Chem., vol. 27, pp. 195–203 (1974).

Haigler et al., Calcofluor White ST Alters the in vivo Assembly of Cellulose Microfibrils, Science, vol. 210, pp. 903–905 (Nov. 21, 1980).

Selitrennikoff, Calcofluor White Inhibits Neurospora Chitin Synthetase Activity, Experimental Mycology, vol. 8, pp. 269–272 (1984).

Roberts et al., Alteration of Cell Wall Assembly in *Oocystis apiculata* by the Fluorescent Brightener Calcofluor White ST., J. Cell Biology, vol. 91, Abstract No. 8050, p. 155a, Nov. 1981.

Herth, Calcofluor White and Congo Red Inhibit Chitin Microfibril Assembly of Poterioochromonas: . . . , J. Cell Biology, vol. 87, pp. 442–450, Nov. 1980.

*Primary Examiner*—Leon B. Lankford, Jr.

*Attorney, Agent, or Firm*—Darryl L. Webster; Gale F. Matthews; Alan M. Gordon

[57] ABSTRACT

The present invention describes a method for inducing epizootic viral infections in insects which consists essentially of potentiating the latent virulence of indigenous insect viruses by contacting the insect with, or applying to its habitat or food supply, a potentiating amount of a stilbene compound. This invention further describes a method for protecting agronomic crops, trees, shrubs, orchards and ornamentals from attack by an insect which employs the application of a stilbene compound to a plant.

20 Claims, No Drawings

POTENTIATION OF EPIZOOTIC VIRAL INFECTIONS OF INSECTS

BACKGROUND OF THE INVENTION

1. Field of the Invention

The present invention relates to the novel use of stilbene compounds to effectively potentiate natural epizootic viral infections of insects as a means of insect control.

2. Description of the Related Art

Although several commercial formulations of entomopathogens (e.g., viruses and bacteria) have been available for many years, their use in agricultural and forestry pest management programs has been rather limited. In general, efficacy of currently available formulations of entomopathogens against pestiferous insects has been considered inadequate due to (1) length of time required to subdue the pest (i.e., unacceptable level of crop-damage may occur before the pest succumbs to factors associated with pathogenic infection) and (2) short residual effectiveness against pest infestation (e.g., stability of entomopathogenic viruses is adversely affected by exposure to ultraviolet solar radiation; Jaques, Can. J. Microbiol., 14: 1161–1163 (1968)).

Doan et al. (J. Insect Pathol., 6: 423–429 (1984)) suggested that greater insect control could occur with the use of viruses if the formulation could be enhanced by the addition of certain adjuvants. Potential virus adjuvants included selected analogs or salts of the stilbene compound, 4,4'-diamino-2,2'-stilbene disulfonic acid. Two such analogs are Calcofluor White and Phorwite (Shapiro et al., published U.S. patent application (USDA), Ser. No. 07/609,848, filed Nov. 7, 1990). Results from several laboratory studies reported by Shapiro et al. demonstrated that Calcofluor White M2R potentiated (as much as 1000-fold) the virulence of the nuclear polyhedrosis virus (NPV) against the gypsy moth larvae, *Lymantria dispar* (as determined by enhanced $LT_{50}$ and $LD_{50}$ values). Shapiro et al., however, made no claims or suggestions regarding the use of stilbene compounds as enhancers of temperate or virulent indigenous viruses. In fact, the stilbene compounds employed alone in the bioassays which are reported in the literature caused no gypsy moth mortality. There have been no reports of insect mortality from the application of the stilbene compounds alone.

Although the mode-of-action pertaining to the stilbene's ability to potentiate the virulence of a virus against an insect is still speculative, there are reports in the literature regarding the biological properties of stilbene compounds. Stilbenes, and at least some of their photoproducts, have been shown to irreversibly bind to proteins in wool, silk, bovine serum albumin and apomyoglobin (Holt et al., Aust. J. Biol. Sci., 27: 23–29 and 195 (1974)). It has been demonstrated that certain stilbene compounds can inhibit cellulose and chitin microfibril formation (Roberts et al., J. Cell Biology, 9: 115a (1981); Herth, J. Cell Biology, 87: 442–450 (1980)). The stilbene, Calcofluor White, prevented formation of cellulose microfibrils in *Acetobacter xylinum* by hydrogen bonding with glucan chains (Haigler et al., Science, 210: 903–906 (1980)) and inhibited chitin synthetase activity in *Neurospora crassa* (Selitrennikoff, Exp. Mycol., 8: 269–272 (1984)). Shapiro et al. found that another stilbene compound, Phorwite AR, synergized a cytoplasmic polyhedrosis virus (CPV) against gypsy moth larvae. Since CPV multiplies only in the midgut epithelial cells, it has been suggested that the site of action of the brightener was the insect's midgut (Dougherty et al., "Mode of Action of Fluorescent Brighteners as Enhancers for the *Lymantria Dispar* Nuclear Polyhedrosis Virus (Ld NPV) in the Gypsy Moth," oral presentation, Am. Society for Virology, Colorado State University, Fort Collins, Colo., Jul. 9, 1991). With the exception of some fluid-feeding species, many insects possess a midgut which is lined with peritrophic membrane, which in turn, is comprised of chitin and protein (Chapman, The Insects Structure and Function, p. 46 (Elsevier, N.Y. 1971)).

It is well known in the art that baculoviruses are abundant in the environment and most of them are existing at very low levels of infection or in an inactive state. For example, a study examining the prevalence of nuclear polyhedrosis viruses (*Trichoplusia ni* (Hübner)) on cabbage revealed that a typical coleslaw serving could contain approximately $10^{10}$ polyhedra per serving. Yet, consumers and insects eat this raw cabbage without undue mortality or disease. Similarly, the gypsy moth nuclear polyhedrosis virus does not appear to be highly and reliably virulent when present in the environment. But applied at high concentrations, the gypsy moth NPV becomes deadly to the insect. Prior entomopathogens with or without the concomitant use of stilbene compounds have focused on applying large lethal concentrations of such viruses to target insects. Therefore, it would be very useful for more effective and safe insect control if the virulence of indigenous insect viruses which are found in nature at cryptic and/or low levels of infection could be potentiated. Furthermore, as a consequence of the instability associated with the prior entomopathogenic viruses in practical use, it is highly desirable to find an inexpensive means for enhancing the latent virulence of the ubiquitous, indigenous insect viruses and inducing epizootic viral infections to effectively control insects.

OBJECTS OF THE INVENTION

It is therefore an important object of the present invention to provide a unique method for inducing epizootic viral infections in insects by creating a virulent state in normally quiescent viruses which would be highly useful in controlling pest insect populations in crops, orchards, forests and the like.

Another object is to provide a new safe and inexpensive method for combatting insects which avoids the undesirable contamination of the environment with chemical and biological agents through potentiating the entomopathogenicity of temperate native insect viruses or virulent native insect viruses at nonlethal concentrations that are already present in the environment.

Further purposes and objects of the present invention will appear as the specification proceeds.

With the foregoing and other objects in view, the invention herein provides a method for inducing epizootic viral infections of insects by treatment of an infested area with a nontoxic stilbene compound. The background of the invention and its departure from the art will be further described hereinbelow.

SUMMARY OF THE INVENTION

The present invention describes a method for potentiating the entomopathogenicity of indigenous insect viruses against insects which utilizes the application of a stilbene compound to control insect populations.

DETAILED DESCRIPTION OF THE INVENTION

In accordance with the present invention, there is provided a novel pesticidal method for enhancing the entomopathogenicity of indigenous insect viruses by treatment of an infested area with a nontoxic stilbene compound. The stilbene compound beneficially potentiates the latent biological virulence of temperate or virulent viruses which are found in nature at cryptic and/or low levels of infections. The method for inducing epizootic viral infections in insects involves contacting the insects with, and/or applying to their habitat or food supply, a potentiating amount of the stilbene compound. The invention also relates to a method for protecting agronomic crops, trees, shrubs, orchards, ornamentals and the like, from attack by insects, by applying to the plants the potentiating amount of the stilbene compound.

Examples of the potentiating agents useful in this invention include, but are not limited to, stilbenes such as triazinylstilbenes (e.g., bistriazinylaminostilbene and the like) or aroylstilbenes such as phenylureidostilbenes (Phorwite RN); etc. For instance, the stilbene compounds would encompass 4,4'-diamino-2,2'-stilbene disulfonic acid; 4,4'-diacetamidostilbene-2,2'-disulfate; 2,2'-(1,2-ethenediyl)bis-[5-(4-phenyl-2H-1,2,3-triazol-2-yl)]-benzenesulfonic acid, dipotassium or disodium salt; 2,2'-(1,2-ethenediyl)bis[5-[4-(4-morpholinyl)-6-(phenylamino)-1,3,5-triazin-2-yl]amino]-benzenesulfonic acid, disodium salt; 2,2'-(1,2-ethenediyl)bis[5-[[4-[(2-hydroxyethyl)-methylamino]-6-(phenylamino)-1,3,5-triazin-2-yl]amino]-benzenesulfonic acid, disodium salt; 2,2'-(1,2-ethenediyl)bis[5-[[4-[bis(2-hydroxyethyl)amino]-6-(phenylamino)-1,3,5-triazin-2-yl]amino]-benzenesulfonic acid, disodium salt; 2,2'-(1,2-ethenediyl)bis[5-[4-methoxy-6-(phenylamino)-1,3,5-triazin-2-yl]amino]-benzenesulfonic acid, disodium salt; 2,2'-(1,2-ethenediyl)bis[5-[(phenylamino)carbonyl]-amino]-benzenesulfonic acid, disodium salt; 2,2'-(1,2-ethenediyl)bis[5-[1,4-dihydro-4-oxo-6-(phenylamino)-1,3,5-triazin-2-yl]amino]-benzenesulfonic acid, disodium salt; 2,2'-(1,2-ethenediyl)bis[5-[[4,6-bis(phenylamino)-1,3,5-triazin-2-yl]amino]-benzenesulfonic acid, disodium salt; etc. Analogs or photoproduct derivatives of the stilbene compounds are contemplated as embraced by this invention. Of course, the conventional salts of each stilbene compound, such as, sulfate, sulfonate, sodium, potassium, ammonium, etc., are also included in the invention.

Preferred potentiating agents are the analogs of 4,4'-diamino-2,2'-stilbene disulfonic acid, namely, a Calcofluor White (available from Sigma Chemical Company, St. Louis, Mo.) such as Calcofluor White M2R, Calcofluor White ABT, Calcofluor White LD, Calcofluor White RWP, etc.; a Blancophor (available from Mobay Chemicals, Pittsburgh, Pa.) such as Blancophor BBH, Blancophor MBBH, Blancophor BHC, etc.; an INTRAWITE® (a heterocyclic stilbene derivative, available from Crompton & Knowles Corp., Charlotte, N.C.) such as INTRAWITE® CF, etc.; a Leucophor (available from Sandoz Chemicals Corp., Charlotte, N.C.) such as Leucophor BS, Leucophor BSB, Leucophor EKB, Leucophor PAB, etc.; a Phorwite (available from Mobay Chemicals, Pittsburgh, Pa.) such as Phorwite AR, Phorwite BBU, Phorwite BKL, Phorwite CL, Phorwite RKK, etc. and the like. Particularly preferred potentiating agents are Phorwite AR and Calcofluor White M2R.

Photoproducts or other derivatives of Calcofluor White, for instance, may encompass the aldehyde, the cis-isomer or the reduced derivative thereof. As a representative compound of the stilbenes, Calcofluor White is usually in the trans-form (I) while the major initial photoproduct is the cis-form (II). The cis-stilbene can be formed from Calcofluor White M2R by room light, sun light, GROW-LUX® light or ultraviolet light from sun light. The conversion in dilute solution (0.02% w/w) is rapid and essentially complete in less than 6 hours of exposure to GROW-LUX® or window light. The aldehyde (III) is prepared from Calcofluor White by permanganate catalyzed periodate oxidation at a pH of 8. The acid (IV) is formed by aerobic oxidation of the aldehyde (III). The reduced compound (V) can be prepared by hydrogenation of Calcofluor White (I) by a 5% aqueous solution of Pd/C with 1N $NH_4OH$. Evaporation of the aqueous solution and extraction of the black residue by warm methanol, filtration and evaporation of the extract gives the reduced compound (V). For illustration, these stilbene compounds are shown below:

-continued

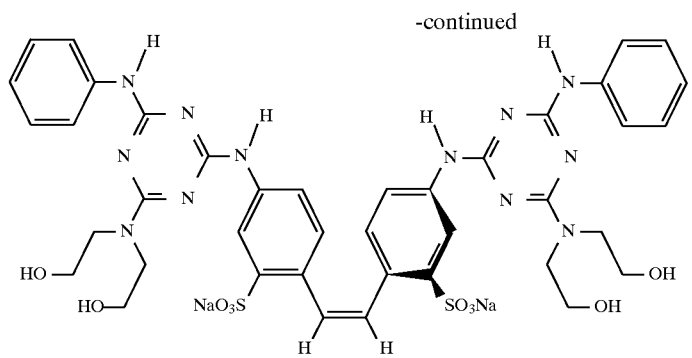

(II)

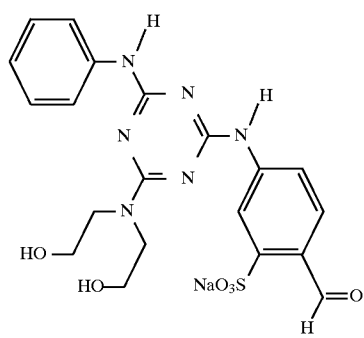

(III)

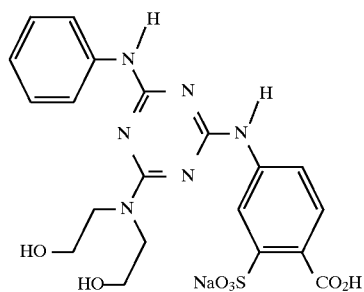

(IV)

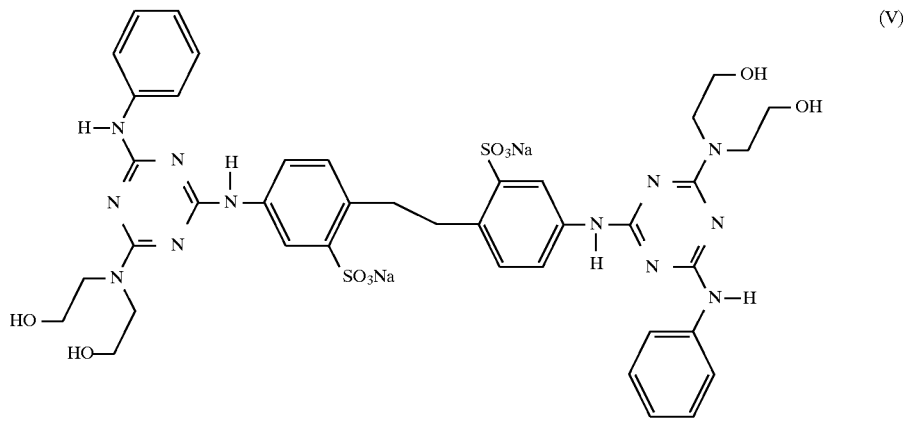

(V)

The compositions of this invention containing the potentiating agent can be applied in either liquid or solid form. Solid form such as dusts or dust concentrates, or liquid form such as emulsifiable concentrates, flowable liquids, aqueous suspension concentrates or wettable powders can be dispersed in water or other inexpensive liquid for application as a finely divided spray. The composition may be applied by conventional methods (e.g., aqueous foliar spray) to row, orchard or ornamental crops for control of insects. Desirably, the formulations which are sprayed onto plants will contain a spray adjuvant to enhance the wetting of the surface to be sprayed and give residual activity of the active ingredient. By affecting surface tension, the spreading agent makes the active compound adhere rapidly to the sprayed plant and prevents loss of the active compound from dew or rainfall. The spray adjuvant can be any conventional spreading agent which enhances the coverage of a treated leaf and the adhesion of the potentiating agent to the leaf such as adhesion agents (commonly known as "stickers"), emulsifiers, wetting agents and the like. Examples of spray adjuvants would include, for example, molasses; petroleum hydrocarbon oils such as EGRIDEX® (an emulsified paraffinic petroleum oil commercially available from Helena Chemical Company, Memphis, Tenn.), etc.; vegetable oils such as soybean oil, etc.; emulsifiers such as polysorbate 80, EMULPHOR® (an ethoxylated castor oil commercially available from Rhone Poulenc, Princeton, N.J.) and the like. Since less of the active ingredient is washed off the plant leaves, the spray adjuvants, in effect, prolong the duration of activity of the stilbene compounds.

Also, the compositions may be prepared in various conventional bait formulations for application to the habitat or food supply of the pests or any area in which the pests may be found. Improved control of the insects can be achieved with treated baits that are distributed in a crop area, pasture, park or other desired location. Baits can be prepared, for example, by admixing the stilbene compound with peanut butter, citrus pulp, apple pumice, wheat-bran, corn meal-sugar, vegetable oils such as soybean oil or other feeding attractants and distributed as is; or these compositions with appropriate adjuvants can be coated onto carriers such as corn cob grits, clays, pumice, synthetic polymer compositions or the like and distributed in the area of the colony. Use of these baits has particular advantage, since such method of distribution poses little or no hazard to animals that may frequent the crop area.

By using the potentiating agent, a product is produced which is highly effective against insects. Advantageously, application of the nontoxic stilbene compound alone avoids the unnecessary cost and ecological consequences of the introduction of toxic chemical and biological agents into the environment to achieve an acceptable level of control of the insects. The compositions manage the insects by potentiation of the latent virulence of indigenous insect viruses that are always present in the environment at either cryptic or sublethal levels of infection. Many insect viruses are erratic in activity. They may be highly pathogenic or virulent but of such low concentration that they do not cause any disease in the insects. The insect viruses may also be cryptic in that they may be carried in colonies, passed along to progeny and perhaps lack activity. With a cryptic insect virus, the insects would present themselves as healthy with little or no mortality and no infection. There would be no reason to believe that the insects have any disease. Yet, after treatment with the stilbene compounds, infectious viruses are unexpectedly recovered from the insects. Surprisingly, the stilbene compound is able to precipitate natural epizootic viral infections in insects.

The present invention is particularly useful for potentiating temperate indigenous insect viruses and virulent indigenous insect viruses which are present at nonlethal concentrations in the environment such as, for example, nuclear polyhedrosis viruses (NPV), cytoplasmic polyhedrosis viruses (CPV), granulosis viruses (GV), entomopox viruses (EPV) and the like. Examples of nuclear polyhedrosis viruses would include *Lymantria dispar* NPV (gypsy moth NPV), *Autographa californica* NPV, *Syngrapha falcifera* NPV (celery looper NPV), *Spodoptera litturalis* NPV, *Mamestra brassicae* NPV, *Choristoneura fumiferana* NPV, *Trichoplusia ni* NPV, *Heliocoverpa zea* NPV, etc. Examples of granulosis viruses would include *Cydia pomonella* GV (coddling moth GV), *Pieris brassicae* GV, *Trichoplusia ni* GV, etc. Examples of entomopox viruses would include *Melolontha melolontha* EPV, *Amsacta moorei* EPV, *Locusta migratoria* EPV, *Melanoplus sanguinipes* EPV, *Schistocerca gregaria* EPV, *Aedes aegypti* EPV, *Chironomus luridus* EPV, etc. It is further contemplated that the present invention will be highly useful in potentiating new insect viruses which are not yet identified and classified in the literature.

Control of insects, particularly the Lepidoptera, Orthoptera, Diptera, Isoptera, Hymenoptera, Homoptera, Hemiptera and Coleoptera orders of insects and protection of agronomic crops, trees, shrubs, orchards and ornamentals from attack by the insects can be achieved by the application of an effective amount of the stilbene compounds to the plants or to the habitat or food supply of the pests. The active ingredient may be applied to the area to be treated in a wide range of useful concentrations. To potentiate the latent virulence of the indigenous insect viruses, the stilbene compound is typically applied at the rate of about 0.01% w/v to about 5.0% w/v, and desirably about 0.1% w/v to about 1.0% w/v. The aforenoted stilbene photoproducts (above compounds identified as formulas II–V) may typically be applied at a similar rate or the lower concentrations around 0.1% w/v. Nevertheless, amounts that are either above or below the specified ranges can also be used, though generally less favorably.

The stilbene compounds are particularly effective in inducing the entomopathogenicity of temperate, native viruses against such pests as tobacco budworms (*Heliothis virescens*), corn earworm also known as bollworm (*Heliocoverpa zea*), old world budworm (*Heliothis armigera*), American budworm (*Heliothis punctigera*), spruce budworm (*Choristoneura fumiferana*), southern armyworm (*Spodoptera eridania*), beet armyworm (*Spodoptera exigua*), fall armyworm (*Spodoptera frugiperda*), tomato pinworm (*Keiferia lycopersicella*), Egyptian cotton leafworm (*Spodoptera litturalis*), armyworm (*Mamestra brassicae*), rootworms (Diabrotica sp.), imported cabbage worm (*Pieris brassicae; Artogeia rapae*), common malarial mosquito (*Aropheles quadrimaculatus*), tarnished plant bug (*Lygris lineolaris*), sweet potato whitefly (*Bemisia tabaci*), western potato leafhopper (*Empoasca abrupta*), green rice leafhopper (*Nephotettix virescens*), rice stem borer (*Chilo supressalis*), European corn borer (*Ostrinia nubalis*), cotton aphid (*Aphis gossypii*), cabbage looper (*Trichoplusia ni* (Hübner)), soybean looper (*Pseudoplusia lugens*), gypsy moth (*Lymantria dispar*), coddling moth (*Cydia pomonella*), diamondbacked moth (*Plutella xylostella*), velvetbean caterpillar (*Anticarsia gemmatalis*), beetle (white grub) (*Popillia japonica*), rhinoceros beetle (*Oryctes rhinoceros*) and male German cockroach (*Blattella germanica*), as well as others.

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

Evaluation of the Stilbene Compounds on Inducing Epizootic Viral Infections in Tobacco Budworms Impact of the stilbene compounds on inducing epizootic viral infections in tobacco budworms (TBW) is determined via a leaf-dip technique. The tobacco budworm colony is well-established twenty-five years ago from field collected insects from Stoneville, Miss. Larvae are reared in individual containers to prevent cannibalism as well as to minimize introduction of entomopathogens. Colony mortality seldom exceeds 1% but occasional spontaneous outbreaks of baculoviral infections do occur. For this reason, a vertical transmission (i.e., through the egg) of an unknown virus causing the infections in this insect colony is suspected. Phenotypically healthy third-instar TBW larvae and technical grade Calcofluor M2R (Sigma Chemical Company, St. Louis, Mo.) are used in this study.

Equal-sized leaves are excised from three-week-old cotton plants which are grown in the greenhouse. Each leaf is immersed in an acetone+water (50+50 parts by volume) solution of a treatment for a period of about three seconds. To promote uniform distribution of the stilbene compound over leaf surfaces, an emulsifier (EMULPHOR® EL620, Rhone Poulenc, Princeton, N.J.) is added to all treatment solutions. EMULPHOR® EL620 comprises 0.1% by volume of each treatment solution. After immersion in the test solutions, leaves are allowed to air-dry for about two hours. Plastic jelly trays are utilized as test arenas in this study. Each tray possesses 50 open-faced cells; dimensions of each cell are 4.0×3.0×1.5 cm (L×W×H). A 2.0×3.0 cm portion of a treated cotton leaf, a moistened (deionized water) cotton fiber dental wick and a phenotypically healthy third-instar TBW larvae are placed in each cell. Jelly tray cells are then covered with a clear plastic sheet, which in turn is sealed over the cells (to prevent larval escape) by using a hot iron. To monitor mortality of TBW larvae due to factors other than treatment intoxication, larvae are placed on leaves treated only with acetone+water+EL620 (i.e., diluent control).

All test arenas are held under constant fluorescent light (GRO-LUX® 40W, Sylvania) and a temperature of 27° C. throughout the post-infestation period. Larval mortality is measured 72 hours after infestation. Moribund larvae (i.e., larvae which are unable to right themselves within 20 seconds after being positioned ventral side up) are classified as dead.

Data obtained are reported in Table I below.

TABLE I

Impact of Calcofluor M2R on Inducing Epizootic Viral Infections in Third-Instar *Heliothis virescens*

| Treatments | N[1,2] | Percent Larval Mortality |
| --- | --- | --- |
| Test 1: | | |
| Diluent Control | 15 | 27 |
| M2R (0.1% w/v) | 14 | 21 |
| M2R (1.0% w/v) | 15 | 46 |
| Test 2: | | |
| Diluent Control | 14 | 0 |
| M2R (0.1% w/v) | 15 | 7 |
| M2R (1.0% w/v) | 15 | 20 |
| Test 3: | | |
| Diluent Control | 20 | 0 |
| M2R (1.0% w/v) | 20 | 25 |

[1]N = number larvae tested, excluding controls.
[2]Larvae used in this study are four to five days old and weigh around 20.9 mg (std. deviation = 4.2).

EXAMPLE 2

Characterization of the New HvNPV Isolate From Diseased Tobacco Budworms

Tobacco budworm cadavers resulting from the treatment of the stilbene compound in Example 1 are examined by microscopy for the presence of entomopathogens. Baculoviral polyhedra are identified in all examined cadavers. Baculoviral polyhedra recovered from the Calcofluor M2R induced TBW are highly infectious to TBW and have a round morphology that differs from the polyhedral morphology of the *Autographa californica* NPV (A.cal).

To determine the genetic origin of the virus which occurs spontaneously and is induced by stilbene compounds in the ARD *Heliothis virescens* colony, a crude number of polyhedral inclusion bodies (PIB) from about 20 diseased tobacco budworms is prepared. All chemical reagents are obtainable from Sigma Chemical Company, St. Louis, Mo., unless specifically noted. Diseased insect larvae are dispersed with a spatula in a small volume of 50 mM Tris–10 mM EDTA–0.1% v/v TRITON® X-100 solution (TRITON® is a mixture of polyoxyethylene ethers commercially available from Sigma Chemical Company), pH of 7.5 (TET) and 20% w/v of sodium deodecyl sulfate (SDS) is added to $\frac{1}{10}$ volume. Large insect fragments settle out by gravity. The supernatant liquid is spun at 350×gravity for 15 minutes to pellet the PIBs. Pellet is resuspended in 3.6 mL of TET and the total number of PIBs (total count=$2.25 \times 10^9$ PIBs) is determined by counting a subsample in a hemocytometer. PIBs are washed by centrifugation and resuspended in 3.6 mL of TET and stored at 4° C. To isolate the DNA, 72 µL of 2N NaOH is added to adjust the pH to about 9.5. Then, 0.4 mL of 1N $Na_2CO_3$ is added to the mixture at room temperature. After a five minute incubation, the PIBs are dissolved. Protein is removed by first neutralizing the mixture with 1.2 mL of 1M Tris-HCl followed by the addition of 140 µL of 20% w/v SDS (final concentration is about 0.5% w/v) and 140 µL of 20 mg/mL pronase from *Streptomyces griseus* (final concentration is about 0.5 mg/mL).

The mixture is allowed to incubate 60 minutes at about 50° C. to digest protein. SDS concentration is adjusted with 0.26 mL of 20% w/v SDS to about a 1.0% w/v SDS concentration, and the final volume of the mixture is adjusted to 8 mL with TET. DNA is extracted twice with equal volumes of water saturated phenol and twice with phenol:chloroform (1:1 ratio). Two volumes of absolute EtOH is added to the aqueous DNA fraction and the DNA is allowed to precipitate overnight at −20° C. DNA is collected by centrifugation at 10,000×gravity for 20 minutes. The DNA pellet is washed once with 70% EtOH and redissolved in 0.4 mL of 20 mM Tris (pH 7.5)–1 mM EDTA. DNA concentration is determined by absorbance at 260 µm. The new virus is designated NPV S1091. Digestion of NPV S1091 and *Autographa californica* NPV-E2 strain with restriction endonuclease Hind III (Boehringer-Mannheim, Indianapolis, Ind.) is set up as per conventional methods. Samples are analyzed on standard 1% w/v agarose gel.

Based on Hind III digestion, the pattern of NPV S1091 is not related to the A.cal-E2 strain. Also, comparison with literature results indicates that NPV S1091 is not related to A.cal-L1 strain. Therefore, NPV S1091 which occurs spontaneously and is induced following stilbene treatment is a distinct isolate from any of the well-known isolates.

Data obtained are reported in Table II below.

TABLE II

Hind III Restriction Endonuclease Digestion Pattern of *Autographa californica* NPV-E2 and NPV S1091

| A.cal NPV-E2 | | NPV S1091 | |
| --- | --- | --- | --- |
| Fragment | Size (KB) | Fragment | Size (KB) |
| A | 21.6 | A | 21.0 |
| B | 20.0 | B | 14.4 |
| C | 11.1 | C | 11.0 |
| D | 9.86 | D | 11.0 |
| E | 9.86 | E | 8.9 |
| F | 8.32 | F | 7.6 |
| G | 8.19 | G | 6.6 |
| H | 5.50 | H | 5.7 |

TABLE II-continued

Hind III Restriction Endonuclease Digestion Pattern
of *Autographa californica* NPV-E2 and NPV S1091

| A.cal NPV-E2 | | NPV S1091 | |
|---|---|---|---|
| Fragment | Size (KB) | Fragment | Size (KB) |
| I | 5.25 | I | 5.0 |
| J | 4.74 | J | 3.4 |
| K | 2.69 | K | 3.0 |
| L | 2.56 | L | 3.0 |
| M | 2.30 | M | 2.6 |
| N | 2.18 | N | 2.5 |
| O | 2.18 | O | 2.4 |
| P | 2.05 | P | 2.0 |
| Q | 2.05 | Q | 1.6 |
| R | 1.79 | | |
| S | 1.66 | | |
| T | 1.02 | | |
| U | 1.02 | | |
| V | 0.90 | | |
| W | 0.77 | | |
| X | 0.64 | | |

EXAMPLE 3

Evaluation of the Stilbene Compounds on Inducing Epizootic Viral Infections in Corn Earworms Impact of the stilbene compounds to induce an epizootic viral infection in bollworm larvae (*Heliocoverpa zea,* Corn earworms) is determined via a diet-overlay technique. Calcofluor M2R is used in this study. Bollworm larvae are obtained from ARS/USDA located at Stoneville, Miss. This bollworm colony is maintained several generations prior to the tests. Despite the most careful efforts to prevent the introduction of entomopathogens, occasional spontaneous outbreaks of a baculoviral infection occurred. For this reason, a vertical transmission (i.e., through the egg) of an unknown virus is suspected. Upon hatching from eggs, larvae are reared for three days on a soybean flour/wheat germ-based diet. Phenotypically healthy three-day-old larvae (i.e., second instars) are used in the study.

The induction of virus in cryptically contaminated bollworms is evaluated via the diet-overlay technique as follows. Plastic bioassay trays, which are manufactured by C-D International Inc. (Pitman, N.J.), are utilized as test arenas. Each tray contains 32 open-faced wells. The dimensions of each well are 4.0×4.0×2.5 cm (L×W×H). A five mL quantity of pinto bean/wheat germ-based diet is poured into each tray-well. After the diet hardened, 0.4 mL of a Calcofluor M2R solution is pipetted onto the diet-surface in each tray-well. Calcof luor M2R solutions are evenly spread over the surfaces of diet by picking up the tray and gently tilting it from side to side. Following application and spreading of treatments, trays are held in a laminar-flow hood for about two hours until water is no longer pooled on diet surfaces. A single, phenotypically healthy three-day-old bollworm is then placed on the surface of diet in each tray-well. After larval infestation, each well is covered with an adhesive, vented clear plastic sheet.

All test arenas are held under constant fluorescent light and a temperature of 27° C. throughout the post-infestation period. Larval mortality is measured every day post-infestation from day 1 to day 9 and again on day 15.

Cadavers are examined by microscopy for the presence of entomopathogens. Baculoviral polyhedra are identified in all examined cadavers. Highly infectious baculoviral polyhedra recovered from dead cadavers have a unique host range specificity. For this reason, it would be clear to those skilled in the art that the stilbene compounds have surprisingly induced lethal infections in bollworm larvae that have been carrying a temperate or cryptic viral infection during serial culture.

Data obtained are reported in Table III below.

TABLE III

Impact of Calcofluor M2R on Inducing Epizootic Viral Infections in Second-Instar *Heliocoverpa zea*

| Treatments | N[1] | Percent Larval Mortality |
|---|---|---|
| Test 1: | | |
| Untreated control | 16 | 0 |
| M2R (0.1% w/v)[2] | 35 | 11 |
| Test 2: | | |
| Untreated control | 16 | 13 |
| M2R (0.1% w/v) | 16 | 44 |

[1]N = number of larvae tested, excluding controls.
[2]Each experiment is replicated twice. The larval mortality of the first sample is measured at 9 days post-infestation and the larval mortality of the second sample is measured at 15 days post-infestation.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

I claim:

1. A method for inducing an epizootic viral infection in an insect which consists essentially of contacting the inset with, or applying to its habitat or food supply, an effective amount of a stilbene compound sufficient for producing the viral infection in the insect which is caused by an indigenous insect virus.

2. The method according to claim 1, wherein the stilbene compound is 4,4'-diamino-2,2'-stilbene disulfonic acid, an analog, a salt or a photoproduct thereof.

3. The method according to claim 2, wherein the stilbene compound is 4,4'-diacetamidostilbene-2,2'-disulfate or an aldehyde, a cis-isomer or a reduced derivative of 4,4'-diamino-2,2'-stilbene disulfonic acid.

4. The method according to claim 2, wherein the analog is a Calcofluor White, a Blancophor, an INTRAWITE®, a Leucophor or a Phorwite.

5. The method according to claim 4, wherein the analog is Calcofluor White M2R or Phorwite AR.

6. The method according to claim 1, wherein the insect is a Lepidoptera, an Orthoptera, a Diptera, an Isoptera, a Hymenoptera, a Homoptera, a Hemiptera or a Coleoptera.

7. The method according to claim 1, wherein the virus is a nuclear polyhedrosis virus, a cytoplasmic polyhedrosis virus, a granulosis virus or an entomopox virus.

8. A method for protecting agronomic crops, trees, shrubs, orchards and ornamentals from attack by an insect which consists essentially of applying to a plant an effective amount of a stilbene compound sufficient for producing an epizootic viral infection in the insect which is caused by an indigenous insect virus.

9. The method according to claim 8, wherein the stilbene compound is 4,4'-diamino-2,2'-stilbene disulfonic acid, an analog, a salt or a photoproduct thereof.

10. The method according to claim 9, wherein the stilbene compound is 4,4'-diacetamidostilbene-2,2'-disulfate or an aldehyde, a cis-isomer or a reduced derivative of 4,4'-diamino-2,2'-stilbene disulfonic acid.

11. The method according to claim 9, wherein the analog is a Calcofluor White, a Blancophor, an INTRAWITE®, a Leucophor or a Phorwite.

12. The method according to claim 11, wherein the analog is Calcofluor White M2R or Phorwite AR.

13. The method according to claim 8, wherein the insect is a Lepidoptera, an Orthoptera, a Diptera, an Isoptera, a Hymenoptera, a Homoptera, a Hemiptera or a Coleoptera.

14. The method according to claim 8, wherein the virus is a nuclear polyhedrosis virus, a cytoplasmic polyhedrosis virus, a granulosis virus or an entomopox virus.

15. A method for protecting agronomic crops, trees, shrubs, orchards and ornamentals from attack by an insect which consists essentially of applying to a plant an effective amount of a stilbene compound sufficient for producing an epizootic viral infection in the insect which is caused by an indigenous insect virus, in combination with a spray adjuvant selected from the group consisting of an adhesion agent, an emulsifier and a wetting agent.

16. The method according to claim 15, wherein the spray adjuvant is a petroleum hydrocarbon oil or a vegetable oil.

17. The method according to claim 15, wherein the spray adjuvant is molasses, an emulsified paraffinic petroleum oil, soybean oil, polysorbate 80 or an ethoxylated castor oil.

18. The method according to claim 15, wherein the stilbene compound is 4,4'-diamino-2,2'-stilbene disulfonic acid, an analog, a salt or a photoproduct thereof.

19. The method according to claim 18, wherein the stilbene compound is 4,4'-diacetamidostilbene-2,2'-disulfate or an aldehyde, a cis-isomer or a reduced derivative of 4,4'-diamino-2,2'-stilbene disulfonic acid.

20. The method according to claim 18, wherein the analog is a Calcofluor White, a Blancophor, an INTRAWITE®, a Leucophor or a Phorwite.

* * * * *